(12) United States Patent
Edginton et al.

(10) Patent No.: US 8,038,645 B2
(45) Date of Patent: Oct. 18, 2011

(54) DEVICE FOR THE TIME-CONTROLLED INTRAVENOUS ADMINISTERING OF THE ANESTHETIC PROPOFOL

(75) Inventors: Andrea Nicole Edginton, Leverkusen (DE); Stefan Willmann, Düsseldorf (DE); Walter Schmitt, Neuss (DE)

(73) Assignee: Bayer Technology Services GmbH, Leverkusen (DE)

( * ) Notice: Subject to any disclaimer, the term of this patent is extended or adjusted under 35 U.S.C. 154(b) by 672 days.

(21) Appl. No.: 11/917,452

(22) PCT Filed: Jun. 3, 2006

(86) PCT No.: PCT/EP2006/005340
§ 371 (c)(1),
(2), (4) Date: Mar. 25, 2008

(87) PCT Pub. No.: WO2006/133825
PCT Pub. Date: Dec. 21, 2006

(65) Prior Publication Data
US 2010/0094202 A1    Apr. 15, 2010

(30) Foreign Application Priority Data
Jun. 17, 2005 (DE) .......... 10 2005 028 080

(51) Int. Cl.
*A61M 31/00* (2006.01)

(52) U.S. Cl. ........................................ 604/66
(58) Field of Classification Search ............ 604/66, 604/503
See application file for complete search history.

(56) References Cited

U.S. PATENT DOCUMENTS

| | | | |
|---|---|---|---|
| 5,609,575 A | 3/1997 | Larson et al. | |
| 5,687,208 A * | 11/1997 | Bae et al. | 378/8 |
| 5,775,330 A * | 7/1998 | Kangas et al. | 600/544 |
| 5,870,697 A * | 2/1999 | Chandler et al. | 702/179 |
| 6,016,444 A * | 1/2000 | John | 600/544 |
| 7,765,092 B2 | 7/2010 | Schmitt et al. | |
| 2004/0172230 A1* | 9/2004 | Willmann et al. | 703/11 |
| 2004/0172330 A1 | 9/2004 | Willmann et al. | |
| 2004/0236554 A1* | 11/2004 | Raghavan et al. | 703/11 |
| 2005/0074803 A1* | 4/2005 | Schmitt et al. | 435/6 |
| 2005/0075274 A1* | 4/2005 | Willmann et al. | 514/1 |
| 2005/0119832 A1* | 6/2005 | Schmitt et al. | 702/19 |
| 2007/0015972 A1* | 1/2007 | Wang et al. | 600/300 |

(Continued)

FOREIGN PATENT DOCUMENTS

DE 10160270 A1 6/2003

(Continued)

OTHER PUBLICATIONS

Munoz H. R., Cortinez L I., Ibacache M. E., Altmann C., Estimation of the plasma effect site equilibration rate constant (ke0) of propofol in children using the time to peak effect. Anesthesiology 2004; 101:1269-74.

(Continued)

*Primary Examiner* — Nicholas D Lucchesi
*Assistant Examiner* — Aarti B Berdichevsky
(74) *Attorney, Agent, or Firm* — Norris McLaughlin & Marcus, P.A.; Christa Hildebrand, Esq.

(57) ABSTRACT

The invention relates to a device for the time-controlled intravenous administering of the anesthetic propofol by means of a method used for determining an adequate dosage profile and adequately controlling an infusion pump as a metering apparatus.

7 Claims, 8 Drawing Sheets

U.S. PATENT DOCUMENTS

| | | | |
|---|---|---|---|
| 2007/0196479 A1* | 8/2007 | Willmann et al. | 424/468 |
| 2007/0196497 A1 | 8/2007 | Pouliquen et al. | |
| 2007/0253903 A1* | 11/2007 | Knab et al. | 424/9.1 |
| 2009/0306944 A1* | 12/2009 | Willmann et al. | 703/2 |

FOREIGN PATENT DOCUMENTS

| | | |
|---|---|---|
| DE | 10345836 A1 | 4/2005 |
| DE | 10345837 A1 | 4/2005 |
| DE | 102004010516 | 9/2005 |
| EP | 1479403 A1 | 4/2004 |
| WO | 2005075274 A1 | 8/2005 |
| WO | 2005084731 A2 | 9/2005 |

OTHER PUBLICATIONS

Gepts E. Camu F., Cockshott I. D., Douglas E. J. Disposition of propofol administered as constant rate intravenous infusions in humans, Anesth Analg 1987, 66(12):1256-63.

Kazama T., Ikeda K., Morita K, Kikura M., Ikeda T., Kurita T. et al, Investigation of effective anesthesia induction doses using a wide range of infusion rates with undiluted and diluted propofol. Anesthesiology 2000, 92(4):1017-28.

Wintermark M., Lepori D., Cotting J., Roulet E., van M. G., Meuli R. et al., Brain perfusion in children: evolution with age assessed by quantitative perfusion computed tomography. Pediatrics 2004; 113(6):1642-52.

Servin F., Farinotti R., Haberer J., Desmonts J., Propofol infusion for maintenance of anesthesia in morbidly obese patients receiving nitrous oxide. Anesthesiology 2005, 78:657-65.

Rigby-Jones A. E., Nolan J. A., Priston M. J., Wright P., Sneyd R., Wolf A. R., Pharacokinetics of propofol infusions in critically ill neonates, infants, and children in an intensive care unit. Antesthesiology 2002, 97:1393-400.

Levitt D. G., Schnider T. W., Human physiologically based pharmacokinetic model for propofol. BMC Anesthesiol. 22. Apr. 2005, 5(1):4.

P. S. Price, R. B. Conolly, C. F. Chaisson, E. A. Gross, J. S. Young, E. T. Mathis, D. R. Tedder, Modeling interindividual variation in physiological factors used in PBPK models of humans, Crit. Rev. Toxicol. 33, 469-503, 2003.

S. Willmann, J. Lippert, M. Sevestre, J. Solodenko, F. Fois, W. Schmitt, PK-Sim, a physiologically based pharmacokinetic whole-body model, Biosilico 1, 121-124, 2003.

Ludbrook G. L., Visco E., Lm A. M., Relation between brain concentrations, electroencephalogram, middle cerebral artery blood flow velocity, and cerebral oxygen extraction during induction of anesthesia, Anesthesiology 2002, 97:1363-70.

Raoof A. A., Van Obbergh L. J., Verbeeck R. K., Propofol pharmacokinetics in children with biliary atresia. Br. J. Anaesth 1995, 74:46-9.

Saint-Maurice C. Cockshott I. D., Douglas E. J., Richard M. O., Harmey J. L., Pharmacokinetics of propofol in young children after a single dose, Br. J. Anaesth 1989, 63(6):667-70.

Valtonen M, Iisalo E., Kanto J., Rosenberg P., Propofol as an induction agent in children, pain on injection and pharmacokinetics. Acta Anaesthesia Sand 1989, 33(2):152-5.

Kanto J., Rosenberg P., Propofol in cesarean section. A pharmacokinetic and pharmacodynamic study, Methods and Findings Experimental Clinical Pharmacology 1990, 12(10)107-11.

Mertens M. J., Olofsen E., Burm A. G., Bovill J. G., Vuyk J., Mixed-effects modeling of the influence of alfentanil on propofol pharmacokinetics, Anesthesiology 2004, 100(4):795-805.

Ickx B., Cockshott I. D., Barvais L., Byttebier G., De P. L., Vandesteene A. et al, Propofol infusion for induction and maintenance of anesthesia in patients with end-stage renal disease, Br. J. Anaesth 1998, 81(6):854-60.

Lysakowski C., Dumont L., Pellegrini M., Clergue F., Tassonyi E., Effects of fentanyl, alfentanil, refentanil and sufentanil on loss of consciousness and bispectral index during propofol induction of anaesthesia. Br. J. Anaesth 2001, 86(4):523-7.

International Search Report dated Sep. 18, 2006.

* cited by examiner

DEVICE FOR THE TIME-CONTROLLED INTRAVENOUS ADMINISTERING OF THE ANESTHETIC PROPOFOL

This is an application filed under 35 USC §371 of PCT/EP2006/005340

BACKGROUND OF THE INVENTION

The invention relates to a device for the time-controlled administration of the anesthetic propofol by means of a procedure for the determination of an appropriate dose profile and corresponding control of an infusion pump acting as a metering unit.

Many medical interventions, particularly invasive surgical interventions, can only be carried out under general anesthesia. Exact time-controlled administration of the anesthetic is crucial to the safety of the patient and the success of the treatment. Ideally, the course of anesthesia should have a rectangular profile, i.e. anesthesia should be induced rapidly at an exactly defined time, then remain approximately constant over a certain period and, after completion of the intervention, be terminated just as quickly. An anesthetic must be administered at an appropriate infusion rate, which varies over time. To this end, medicine uses electronically controlled infusion pumps, which permit programming of the infusion rate. However, this is complicated by the fact that the time/effect profile of the anesthetic, which determines the course of anesthesia, is influenced both by the infusion rate and by a series of patient-related anatomical, physiological, biochemical, and genetic factors. As soon as the anesthetic enters the patient's systemic circulation the substance undergoes distribution in the body. The anesthetic is transported in the bloodstream to various organs, where it finally passes into the cells. These organ distribution kinetics are determined e.g. by the individual blood flow rates in the different organs, which can be substantially different from typical healthy adults in certain subpopulations (e.g. children, the elderly, diseased patients, pregnant women). In addition, the clearance, that is the rate of metabolism in the excretory organ (mostly the liver, in part other organs such as the intestine or kidney as well), determines the elimination kinetics, which are of central significance to the maintenance and termination of the anesthesia. This clearance is also highly dependent on individual factors in the patients concerned, e.g. age, sex, level of expression of metabolizing enzymes and rate of blood flow through the eliminating organ.

From a pharmacodynamic viewpoint, it is the time course of the concentration of the anesthetic at its site of action, the brain, which is of particular interest, as this determines the course of anesthesia.

Computer-controlled infusion pumps with input functions determined using a pharmacokinetic model are known from the prior art and are commercially available under the term "TCI" (=target controlled infusion). The main application of TCI is the control of intravenous administration of the anesthetic propofol.

U.S. Pat. No. 5,609,575 describes a TCI system in which the dose-concentration routine uses the body weight index as the only patient parameter in the system and only achieves a rough simulation of the concentration. There is a commercial system for the control of infusion pumps for the anesthetic propofol, marketed as Diprifusor™ from AstraZeneca— product information "Diprifusor™: Target Controlled Infusion (TCI) in anaesthetic practice", AstraZeneca Anaesthesia, New Edition (1998). Another infusion system specifically for use in children is in development (Paedfusor, Munoz H R, Cortinez L I, Ibacache M E, Altmann C. Estimation of the plasma effect site equilibration rate constant ($k_{e0}$) of propofol in children using the time to peak effect. Anesthesiology 2004; 101:1269-74). In the prior art, the pharmacokinetic profile of propofol, i.e. its spread and distribution as a function of time after administration, is described by an open three-compartment model (Gepts E, Camu F, Cockshott I D, Douglas E J. Disposition of propofol administered as constant rate intravenous infusions in humans. Anesth Analg 1987; 66(12):1256-63; Munoz H R, Cortinez L I, Ibacache M E, Altmann C. Estimation of the plasma effect site equilibration rate constant (ke0) of propofol in children using the time to peak effect. Anesthesiology 2004; 101:1269-74). The central compartment in this three compartment model represents the blood pool, one peripheral compartment is the so-called "effect compartment" which describes the time course of the concentration of the anesthetic at its site of action, and the third compartment represents organs with low blood perfusion, which cause slow redistribution of the anesthetic, which affects its elimination. Patient-related input parameters in this system are the age, body weight and a target concentration in the patient's blood. The infusion rate to be used is calculated from these on the basis of an open three-compartment model fitted to experimental data. The parameters in this three-compartment model (volumes of the compartments, mass-transfer rates, and elimination rates) are age and/or body-weight dependent. Of central significance to the entire system is the transport rate between the central (blood) compartment and the effect compartment ($k_{e0}$), which ultimately regulates the time course of propofol at its site of action and thus the course of anesthesia. Several such parameter sets for propofol have been published in the literature (Kazama T, Ikeda K, Morita K, Kikura M, Ikeda T, Kurita T et al. Investigation of effective anesthesia induction doses using a wide range of infusion rates with undiluted and diluted propofol. Anesthesiology 2000; 92(4):1017-28; Munoz H R, Cortinez L I, Ibacache M E, Altmann C. Estimation of the plasma effect site equilibration rate constant ($k_{e0}$) of propofol in children using the time to peak effect. Anesthesiology 2004; 101:1269-74). The underlying three-compartment model can be found on the internet and is publicly accessible (TIVA-Trainer, available under www.eurosiva.org).

The disadvantage of this known device is that these fitted model parameters are only average values representing the patients in the underlying experimental study. Although these models can take into account the dependency of the parameters on body weight and, in part, age as well, there is no possibility of more extensive individualization and adjustment of the pharmacokinetic model parameters to specific patients. Thus, the open three-compartment models described are unable to allow for the physiological peculiarities of specific patient groups, e.g. children or the elderly or diseased patients. An example of this is the nonlinear age-dependency of blood flow in the brain (the target organ of propofol) in children. The body-weight-normalized blood flow rate in a two-year-old child is twice as high as in a five-year-old child (Wintermark M, Lepori D, Cotting J, Roulet E, van M G, Meuli R et al. Brain perfusion in children: evolution with age assessed by quantitative perfusion computed tomography. Pediatrics 2004; 113(6):1642-52), a fact which cannot be described by an age-independent mass-transfer rate in the effect compartment ($K_{e0}$). Equally, age-related differences in the composition of the body (in respect of its relative proportions of water, fat, and protein) very substantially influence the volume of distribution, and thus the kinetics, of propofol. Similarly, the pharmacokinetics of propofol in obese patients does not just depend on the body weight, but rather the proportion of fat. In the elderly and in diseased patients—but also in children—differences in the metabolic rate decisively influence the propofol level in the blood and brain. The volume of the central compartment is similar in obese and normal-weight people, which can be explained by the comparatively low variability of the volume of well-perfused tissue between such individuals. On the other hand, the peripheral compartments, in particular that which represents poorly perfused tissue, are distinctly different, which leads to a larger volume of distribution in the obese. As a result, the times for the induction of general anesthesia are similar, but recovery is faster in obese patients (Servin F, Farinotti R, Haberer J, Desmonts J. Propofol infusion for maintenance of anesthesia in morbidly obese patients receiving nitrous oxide. Anesthesiology 2005; 78:657-65). Behavior similar to that in the obese has been observed in neonates, in whom the volume of the peripheral compartment is also relatively larger than that in adults, which can be explained by the relatively high proportion of body fat in neonates. Neonates also wake more quickly from general anesthesia after the end of propofol infusion, but they recover only relatively slowly from the sequelae, which can be attributed to a reduced systemic clearance (Rigby-Jones A E, Nolan J A, Priston M J, Wright P, Sneyd R, Wolf A R. Pharmacokinetics of propofol infusions in critically ill neonates, infants, and children in an intensive care unit. Anesthesiology 2002; 97:1393-400).

The influence of such physiological, anatomical, and biochemical or genetic peculiarities on the course of anesthesia is only inadequately described with the device known from the prior art. The use of an open three-compartment model limits the flexibility to take into account different conditions of the patient such as age-dependent differences in body composition, blood flow rates and the metabolic rate, obesity, or pregnancy, etc.

Lewitt et al. describe a physiology-based pharmacokinetic model for the simulation of plasma pharmacokinetics of propofol after intravenous administration (Levitt D G, Schnider T W., Human physiologically based pharmacokinetic model for propofol. BMC Anesthesiol. 2005 Apr. 22; 5(1):4). The model provides a good description of the concentration/time course of propofol in the plasma of adult patients, but does not describe the extent to which the concentrations in the brain calculated using the model reflect the actual time course of the effect of propofol. The usefulness of this model is further limited by the fact that only the fat content of the patient based on an empirical correlation equation and the propofol clearance are included as individual parameters. More extensive patient-individual parameterization is not performed. In particular, individual differences in the blood flow rates to peripheral organs, which have a substantial influence on the entire distribution kinetics of substances with rapid distribution such as propofol, are not taken into account. Simulation of the propofol pharmacokinetics in children using the model published by Levitt et al. is not possible either, as the model only describes average physiological parameters for adults. Furthermore, Lewitt et al. only describe a model for the simulation of plasma pharmacokinetics of propofol, not a device for the time-controlled administration of propofol.

The purpose of the invention is to develop an improved device, starting from the prior art described, which would permit exact time-controlled administration of propofol taking into account individual physiological, anatomical, biochemical, and genetic factors of the patient.

BRIEF SUMMARY OF THE INVENTION

The invention therefore relates to a device which uses a PBPK/PD model to determine an optimal time course of the administration for the individual patient by iterative adjustment either of the concentration/time course in the brain or the pharmacodynamic effect/time course to a specified time target profile. This optimized time course for the administration is then used as an input function for a dose metering device. In combination with real-time measurements of physiological parameters, a closed regulatory cycle can be created which is substantially better than the black-box device cited as prior art which does not make use of physiological knowledge.

The most important characteristic of the invention consists in combination of a physiology-based pharmacokinetic and/or pharmacodynamic model (PBPK/PD) with an automatic dose metering device, e.g. an electronically controlled infusion pump. PBPK/PD models have advantages over non-physiological compartment models, because they can describe the influence of individual physiological, anatomical, biochemical, and genetic factors on the pharmacokinetics and pharmacodynamics in detail.

BRIEF DESCRIPTION OF THE DRAWINGS

In the drawings, wherein like reference numerals delineate similar elements throughout the several views.

DETAILED DESCRIPTION OF THE PRESENTLY PREFERRED EMBODIMENTS

Figure 1:
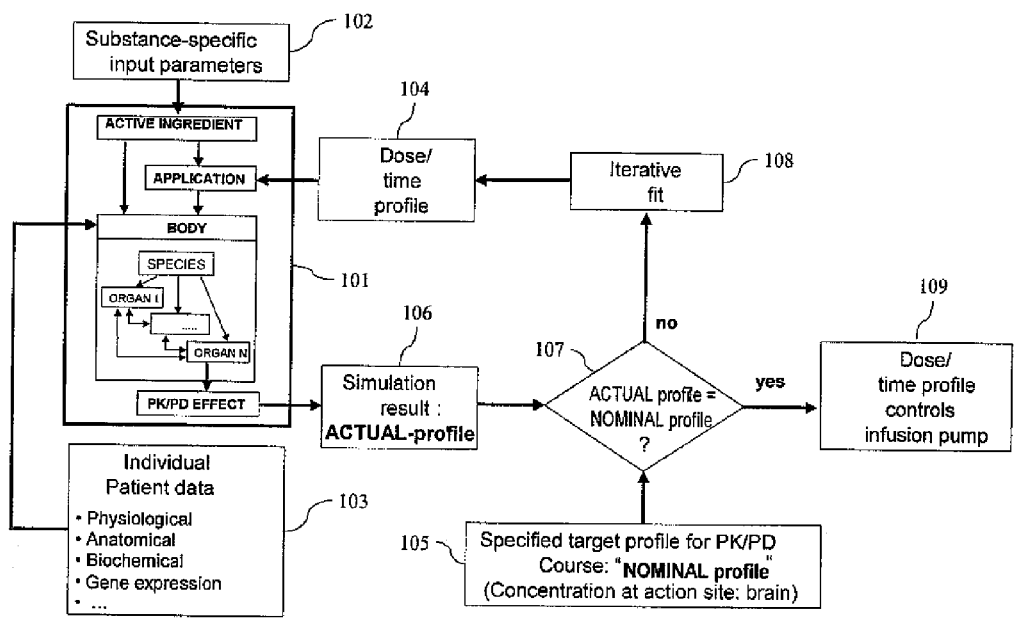
FIG. 1: Schematic representation of the device for the time-controlled administration of anesthetics

A schematic representation of the inventive device is given in FIG. 1, The main component is a PBPK/PD model (101)

which describes a mammalian (in particular human) body and which requires a number of different parameters as input values:

1.) Substance-specific parameters of the anesthetic to be administered (102). Typical substance-specific parameters include physicochemical parameters such as lipophilicity, binding constants to human serum albumin and/or other plasma proteins, unbound plasma fraction, solubility in aqueous buffer solution or in intestinal juice, the size of the molecule (expressed as molecular weight or molar volume), hepatic and/or renal clearance, permeability coefficients e.g. via artificial or biological membranes, and equilibrium distribution coefficients between plasma (or blood) and the various organs.

2.) Species-specific physiological, anatomical, biochemical, and/or genetic input parameters which are characteristic of the patient concerned (103). These types of parameters include, in particular, body weight, volume proportions of individual organs relative to the total body volume, blood flow rates in individual organs, proportions of water, fat, and lipid in individual organs, as well as parameters which characterize the expression and function of metabolically active enzymes (particularly in the liver and intestine) or the expression and function of proteins for the active transport of molecules through cell membranes. These parameters can either be measured directly or they correlate, for certain populations, with easily measured patient parameters such as age, sex, body weight and lean body mass (P. S. Price, R. B. Conolly, C. F. Chaisson, E. A. Gross, J. S. Young, E. T. Mathis, D. R. Tedder: "Modeling interindividual variation in physiological factors used in PBPK models of humans", *Crit. Rev. Toxicol.* 33, 469-503 (2003)). Some or several of these parameters can be used in the inventive procedure. It is also possible that some or several of these parameters, such as blood flow rates, change over time, so that it is sensible to take these changes into account during the simulation.

3.) A dose profile, which describes the dose administered as a function of time (104).

In addition, the following are specified:

4.) A target profile, showing the desired concentration/time course of the anesthetic to be administered in plasma, blood, or directly at the biochemical target in the target organ, or the desired effect/time course ("NOMINAL profile", 105). In the case of the administration of anesthetics, a rectangular effect profile with the steepest possible flanks is the objective, i.e. the desired anesthetic effect should start spontaneously, remain as constant as possible over a defined period, then rapidly subside again at the end of treatment. The target profile can either be a simple time function $Z(t)$ or—alternatively or additionally—a tolerance range (defined as an interval with a maximum and minimum value $[Z_{min}(t) \ldots Z_{max}(t)]$).

Starting from a sensibly chosen start function for the dose profile, the PBPK/PD model uses the information from 1.) and 2.) to calculate the individual concentration/time profile or effect/time profile for the substance under consideration ("ACTUAL profile", 106).

In principle, it is possible to consider different routes of administration of the anesthetic using the PBPK/PD model. Intravenous administration is particularly important and preferred.

With the aid of an iterative optimization process, the administration profile is varied until the simulated concentration/time profile or effect/time profile matches the NOMINAL profile (107, 108). As a result of this numerical optimization, a time/dose profile is obtained which shows the desired concentration/time or effect/time course for the substance under consideration in the individual patient or which shows the least deviation from this. Possible numerical optimization procedures include gradient procedures, gradient-free procedures, stochastic procedures or evolutionary procedures. Particularly favored gradient procedures are the quasi-Newton or Newton procedure and, among the gradient-free procedures, especially the nested-intervals procedure. Among the stochastic methods, the Monte-Carlo procedure is preferred in particular, the genetic optimization method is a particularly favored form of an evolutionary procedure.

This dose profile is used in the last step to control an automatic dose metering device.

Accordingly, this invention also relates to a device for the time-controlled administration of the anesthetic propofol, characterized in that it has:
  a) a substance-dependent target profile, which shows a desired concentration/time course in the brain or a desired effect/time course,
  b) a physiology-based pharmacokinetic and/or pharmacodynamic simulation with a dose profile which is variable over time taking into account individual parameters of the patient and substance-specific input parameters of the anesthetic to be administered,
  c) an iterative numerical fit of the dose profile until the simulated time profile agrees with the specified target profile or shows the maximum achievable agreement with it, with
  d) a metered dose device controlled on the basis of the result of c).

In certain cases, it may be sensible not simply to regulate the dose metering device on the basis of the desired pharmacokinetic or pharmacodynamic target profile, but to include an external measured parameter, e.g. parameters derived from an electroencephalogram (EEG), as additional input parameters. In a particular embodiment, the depth of anesthesia is also monitored on-line by one or more suitable sensors and the measured signals are integrated into the procedure as additional input parameters. Control of the dose metering device is then not purely regulated by the pharmacodynamic or pharmacokinetic time profile, but also draws on external measured signals. Thus, for example, the dose of anesthetic can be increased if the measured depth of anesthesia falls below a critical level. In this way, it is possible to create a closed regulatory cycle, which optimizes the dose of anesthetic as a function of time in real time on the basis of on-line measurements and physiological simulations. Possible on-line measurements could include parameters obtained with the aid of an electroencephalogram (EEG), for example the bispectral index (BIS). In this embodiment, the known response of the pharmacodynamic or pharmacokinetic profile from the physiological simulation is used to change the rate of administration, in order to readjust the rate of anesthetic administration to the requirements of the patient, as indicated by the sensor. In another special embodiment, the signal from the sensor on its own is used for regulation for a short time if there is a critical condition (e.g. if there is a risk of the patient waking prematurely from anesthesia).

Any of the named parameter-based procedures is in principle suitable for use as the simulation procedure, and the procedures claimed in DE-A-10160270 and DE-A-10345836 and corresponding physiology-based PK/PD models are particularly suitable and preferred in terms of the invention (marketed as PK-Sim®—www.PK-Sim.com; S. Willmann, J. Lippert, M. Sevestre, J. Solodenko, F. Fois, W. Schmitt: "PK-Sim®: a physiologically based pharmacokinetic 'whole-body' model", *Biosilico* 1, 121-124 (2003)). This simulation procedure takes into account the influence of individual physiological and anatomical parameters such as organ size and composition, blood flow rates, etc. on the pharmacokinetic behavior of medicinal products as a function of time. These physiological and anatomical parameters can be derived from a few easily measured parameters such as body weight and body mass index. In addition, these parameters are age-, sex-, and sometimes race-dependent. DE-A-10 345 837 has also described how biochemical and genetic information, e.g. expression data on metabolically active enzymes or active transporters, can be used to determine a dose individually tailored to the patient.

One study has shown that the concentration/time course of the anesthetic propofol at the site of action calculated with PK-Sim® actually is predictive of the course of anesthesia (S. Willmann et al.: "A pharmacodynamic extension for the physiology-based pharmacokinetic whole-body model PK-Sim®" Poster at EUFEPS 2004, Brussels, 17.-20.10.2004). This study was based on experimental data from LUD-BROOK et al. (Ludbrook G L, Visco E, Lm A M.: "Relation between brain concentrations, electroencephalogram, middle cerebral artery blood flow velocity, and cerebral oxygen extraction during induction of anesthesia" Anesthesiology 2002; 97:1363-70), who determined the concentration/time profile of propofol in plasma after intravenous administration of together with the bispectral index (BIS), a parameter derived from the EEG which is a measure of the depth of anesthesia. In this case, the measured plasma concentration/time course did not correlate with the time course of anesthesia. If BIS is plotted as a function of the plasma concentration, a hysteresis curve is obtained (S. Willmann et al.: "A pharmacodynamic extension for the physiology-based pharmacokinetic whole-body model PK-Sim®" Poster at EUFEPS 2004, Brussels, 17.-20.10.2004). Simulation of propofol pharmacokinetics with PK-Sim® gave very good agreement with the plasma concentration. Interestingly, the simulated active substance concentration in the brain relative to the plasma showed a slower build-up of propofol, which is in good temporal agreement with the BIS profile. If the BIS value obtained experimentally by Ludbrook et al. (Ludbrook G L, Visco E, Lm A M.: "Relation between brain concentrations, electroencephalogram, middle cerebral artery blood flow velocity, and cerebral oxygen extraction during induction of anesthesia" Anesthesiology 2002; 97:1363-70) is plotted as a function of active substance concentration in the brain predicted by PK-Sim®, the hysteresis collapses, which is strong evidence of the predictive nature of the simulated brain profile in respect of the pharmacodynamic effect of anesthesia (S. Willmann et al.: "A pharmacodynamic extension for the physiology-based pharmacokinetic whole-body model PK-Sim®" Poster at EUFEPS 2004, Brussels, 17.-20.10.2004).

This simulation procedure in combination with a dose metering device makes possible the desired time-controlled administration of propofol allowing for individual physiological, anatomical, biochemical, and genetic factors of the patient.

The target group for the use of the inventive device includes humans and mammals, in particular livestock, breeding animals, laboratory animals, test animals, and pets. The procedure is particularly preferred for use as an aid in the therapeutic treatment of humans or in clinical studies in humans.

The livestock and breeding animals include mammals such as cattle, horses, sheep, pigs, goats, camels, water buffaloes, donkeys, rabbits, fallow deer, reindeer, and animals raised for fur, e.g. mink, chinchilla, or raccoon.

The laboratory and test animals include mice, rats, guinea pigs, hamsters, rabbits, dogs, cats, pigs, and monkeys of all species, sub-species, and breeds.

The pets in particular comprise cats and dogs.

The possible electronically controlled dose metering devices include, in particular, electronically controlled infusion pumps.

Example

The application example is based on simulations with the commercially available physiology-based pharmacokinetic model PK-Sim® developed by Bayer Technology Services GmbH and the TIVA-Trainer Diprifusor™ software published and available on the internet. The following values for propofol were used as substance-dependent input parameters for PK-Sim® (Table 1):

TABLE 1

| PARAMETER | VALUE |
| --- | --- |
| Lipophilicity | 2.6 |
| Molecular weight | 178 |
| Free plasma fraction (age-dependent) | 0.020-0.025 |
| Clearance (age-dependent) | 29-50 ml/min/kg |

Initial simulations with PK-Sim® have shown that the diffusion through the cell membranes in organs is faster than would be expected for a molecule with these physicochemical properties. To compensate for this effect, all organ-specific permeability coefficients in PK-Sim® were multiplied by a factor of 20, so that distribution into peripheral compartments is limited purely by the blood flow rates.

First it is shown that it is possible in principle to use PK-Sim® to describe the plasma-concentration/time course of propofol in a number of different individuals correctly on the basis of the values and assumptions cited above. To do this, literature data on the plasma-concentration/time course of propofol were collected and compared with the results of simulations with PK-Sim° and the Diprifusor™ model (TIVA-Trainer). Pharmacokinetic and/or pharmacodynamic data from children (Valtonen M, Iisalo E, Kanto J, Rosenberg P. Propofol as an induction agent in children: pain on injection and pharmacokinetics. Acta Anaesthesiol Scand 1989; 33(2): 152-5; Raoof A A, Van Obbergh L J, Verbeeck R K. Propofol pharmacokinetics in children with biliary atresia. Br J Anaesth 1995; 74:46-9; Saint-Maurice C, Cockshott I D, Douglas E J, Richard M O, Harmey J L. Pharmacokinetics of propofol in young children after a single dose. Br J Anaesth 1989; 63(6):667-70), young adults (Mertens M J, Olofsen E, Burm A G, Bovill J G, Vuyk J. Mixed-effects modeling of the influence of alfentanil on propofol pharmacokinetics. Anesthesiology 2004; 100(4):795-805), normal-weight and obese adults (Ickx B, Cockshott I D, Barvais L, Byttebier G, De P L, Vandesteene A et al. Propofol infusion for induction and maintenance of anaesthesia in patients with end-stage renal disease. Br J Anaesth 1998; 81(6):854-60; Servin F, Farinotti R, Haberer J, Desmonts J. Propofol infusion for maintenance of anesthesia in morbidly obese patients receiving nitrous oxide. Anesthesiology 2005; 78:657-65; Lysakowski C, Dumont L, Pellegrini M, Clergue F, Tassonyi E. Effects of fentanyl, alfentanil, remfentanil and sufentanil on loss of consciousness and bispectral index during propofol induction of anaesthesia. Br J Anaesth 2001; 86(4):523-7; Kazama T, Ikeda K, Morita K, Kikura M, Ikeda T, Kurita T et al. Investigation of effective anesthesia induction doses using a wide range of infusion rates with undiluted and diluted propofol.

Anesthesiology 2000; 92(4):1017-28; Kazama T, Morita K, Ikeda T, Kurita T, Sato S. Comparison of predicted induction dose with predetermined physiologic characteristics of patients and with pharmacokinetic models incorporating those characteristics as covariates. Anesthesiology 2003; 98(2):299-305), and pregnant women (Kanto J, Rosenberg P. Propofol in cesarean section. A pharmacokinetic and pharmacodynamic study. Methods and Findings in Experimental Clinical Pharmacology 1990; 12(10):707-11.) were compared. An overview is given in the table below:

TABLE 2

Pharmacokinetic studies of propofol in various patient populations

| Study | Age in years: mean (range) | Body weight in kg: mean (std. dev.) | Dose | Blood clearance in ml/min: mean (std. dev.) |
|---|---|---|---|---|
| Raoof et al. | 1.9 (0.92 to 3.6) | 10.6 (2.1) | 3 mg/kg | 38.7 (6.8) |
| Saint-Maurice et al. | 5.5 (1.08) | 19.3 (2.35) | 2.5 mg/kg bolus over 0.33 min | 30.6 (2.9) |
| Valtonen et al. | 6.5 (3 to 10) | 23.7 (16 to 33) | 2.5 mg/kg bolus over 0.5 min | 32.0 (16.8) |
| Kanto et al. | 27.1 (4.3) 100% women | 84.3 (12.3) | 2.5 mg/kg bolus over 0.17 min | 27.5 (5.5) |
| Mertens et al. | 24 (20 to 30): 100% men | 70.0 (4) | 1 mg/kg bolus over 1 min, then 3 mg/kg/h | 31.2 (2.8) |
| Ickz et al. | 45.2 men/women = 4/5 | 72.6 (7) | 21 mg/kg/h for 5 min, then 12 mg/kg/h for 10 min, then 6 mg/kg/h | 33.8 (7.8) |

Figure 2:
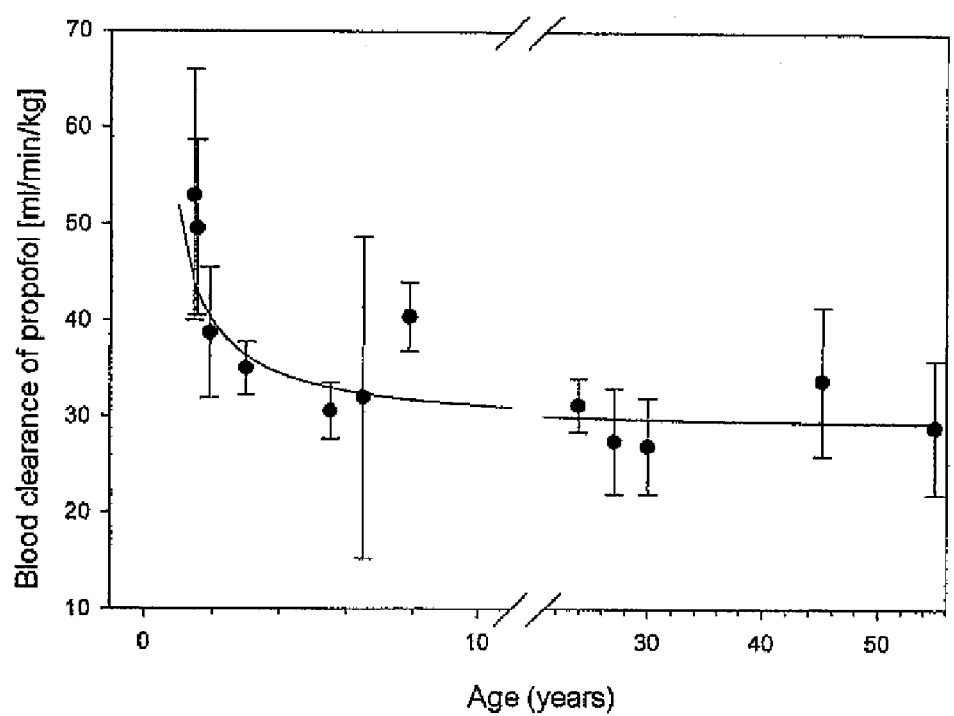
FIG. 2: Age dependency of propofol clearance (symbols: experimental data from the literature; line: least square fit)

The "Create Individual" function in PK-Sim® makes possible the simulation of a virtual individual, characterized by citing the age, sex, race (various races are specified) and two parameters selected from the body weight (BW), body mass index (BMI) or height (H) (these three parameters are related by the equation $BMI=BW/H^2$). Another important input parameter is the clearance, that is the rate of elimination of the substance. Propofol is metabolized in the liver. The activity of the metabolizing enzymes is known to be age-dependent. FIG. 2 shows a fit (line) through experimental data (symbols) which describe propofol clearance as a function of age. The "Create Individual" function was used to simulate the studies cited in Table 2. These cases were also simulated using the TIVA-Trainer Diprifusor™ software and, in the case of the pediatric study, the Paedfusor model.

Figure 3:
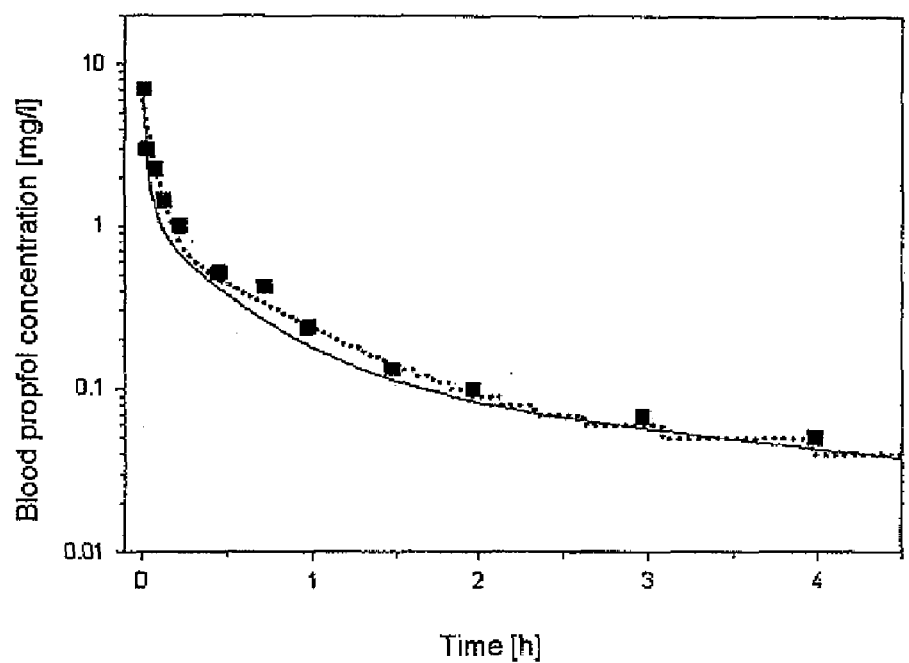
FIG. 3: Predicted (lines) and experimental (symbols, data from Raoof et al.) blood propofol concentrations after intravenous administration in children (mean age 1.9 years). The continuous line represents the concentrations calculated by PK-Sim®, the dotted line those calculated by TIVA-Trainer.

FIG. 3 shows the predicted (lines) and experimental (symbols, data from Raoof A A, Van Obbergh L J, Verbeeck R K. Propofol pharmacokinetics in children with biliary atresia. Br J Anaesth 1995; 74:46-9) blood propofol concentrations after intravenous administration in children (mean age 1.9 years).

Figure 4:
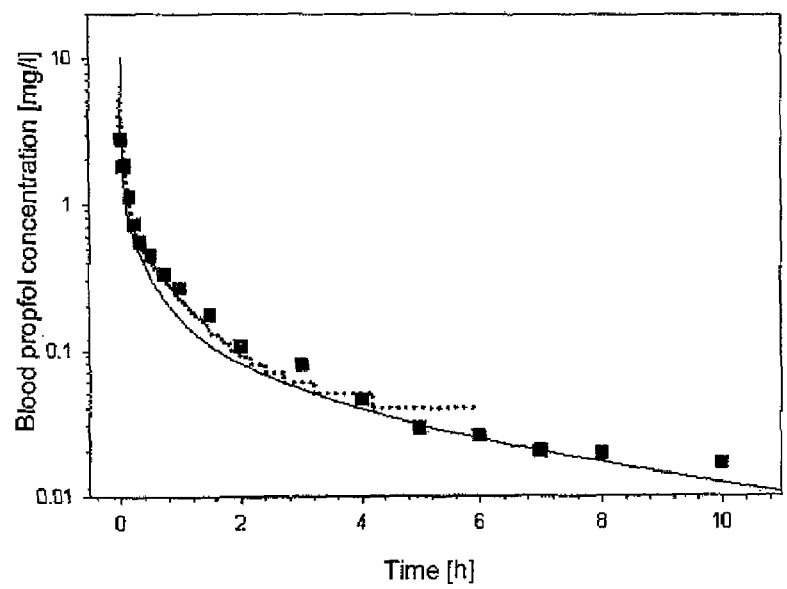
FIG. 4: Predicted (lines) and experimental (symbols, data from Saint-Maurice et al.) blood propofol concentrations after intravenous administration in children (mean age 5.5 years). The continuous line represents the concentrations calculated by PK-Sim®, the dotted line those calculated by TIVA-Trainer.

FIG. 4 shows the predicted (lines) and experimental (symbols, data from Saint-Maurice C, Cockshott I D, Douglas E J, Richard M O, Harmey J L. Pharmacokinetics of propofol in young children after a single dose. Br J Anaesth 1989; 63(6): 667-70.) blood propofol concentrations after intravenous administration in children (mean age 5.5 years).

Figure 5:
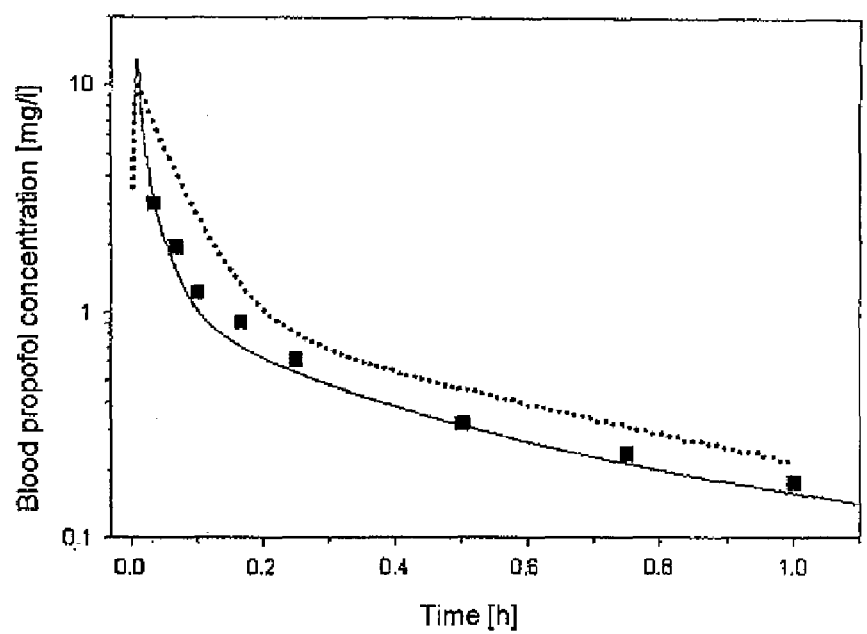
FIG. 5: Predicted (lines) and experimental (symbols, data from Valtonen et al.) blood propofol concentrations after intravenous administration in children (mean age 6.5 years). The continuous line represents the concentrations calculated by PK-Sim®, the dotted line those calculated by TIVA-Trainer.

FIG. 5 shows the predicted (lines) and experimental (symbols, data from Valtonen M, Iisalo E, Kanto J, Rosenberg P. Propofol as an induction agent in children: pain on injection and pharmacokinetics. Acta Anaesthesia) Scand 1989; 33(2): 152-5) blood propofol concentrations after intravenous administration in children (mean age 6.5 years).

Figure 6:
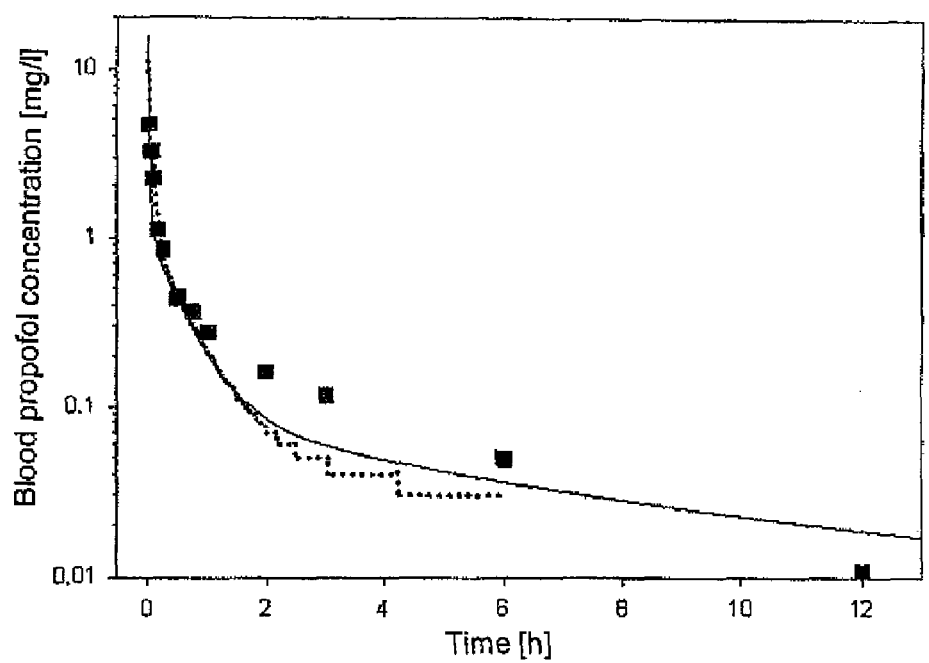
FIG. 6: Predicted (lines) and experimental (symbols, data from Kanto et al.) blood propofol concentrations after intravenous administration in pregnant women (mean age 27.1 years). The continuous line represents the concentrations calculated by PK-Sim®, the dotted line those calculated by TIVA-Trainer.

FIG. 6 shows the predicted (lines) and experimental (symbols, data from Kanto J, Rosenberg P. Propofol in cesarean section. A pharmacokinetic and pharmacodynamic study. Methods and Findings Experimental Clinical Pharmacology 1990; 12(10):707-11.) blood propofol concentrations after intravenous administration in pregnant women (mean age 27.1 years).

Figure 7:
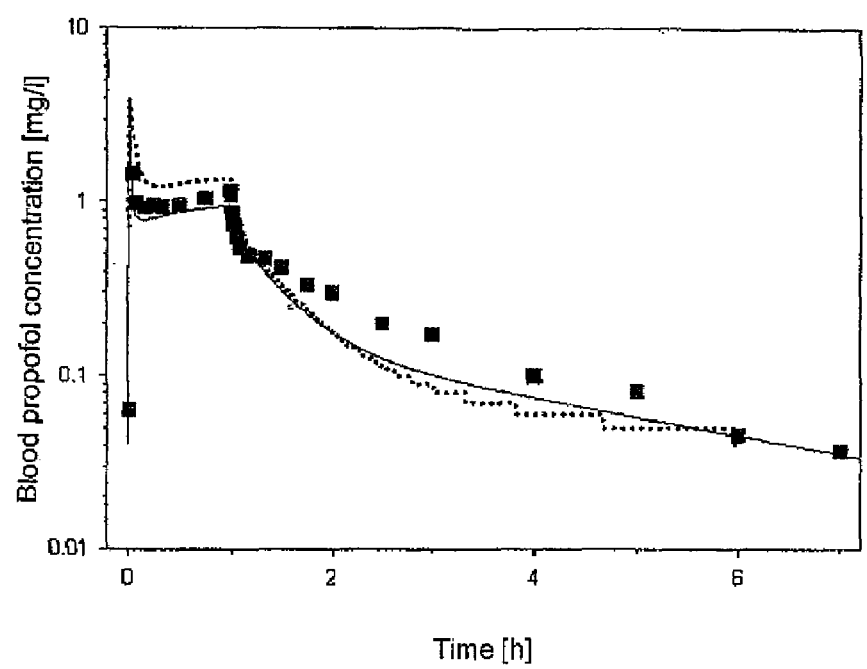
FIG. 7: Predicted (lines) and experimental (symbols, data from Mertens et al.) blood propofol concentrations after intravenous administration in young men (mean age 24 years). The continuous line represents the concentrations calculated by PK-Sim®, the dotted line those calculated by TIVA-Trainer.

FIG. 7 shows the predicted (lines) and experimental (symbols, data from Mertens M J, Olofsen E, Burm A G, Bovill J G, Vuyk J. Mixed-effects modeling of the influence of alfentanil on propofol pharmacokinetics. Anesthesiology 2004; 100(4):795-805.) blood propofol concentrations after intravenous administration in young men (mean age 24 years).

Figure 8:
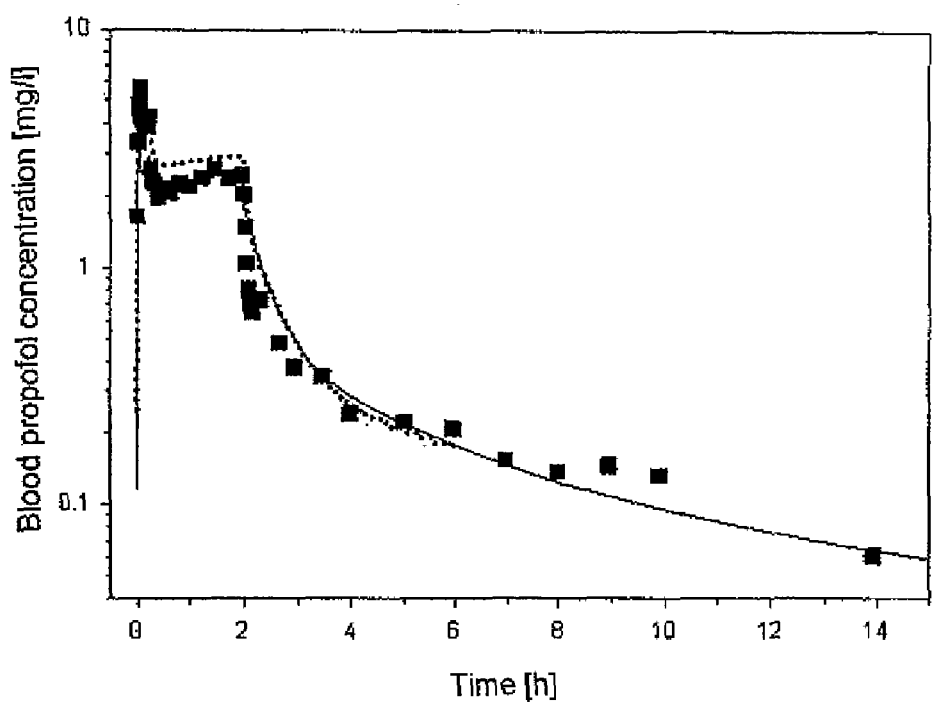
FIG. 8: Predicted (lines) and experimental (symbols, data from Ickx et al.) blood propofol concentrations after intravenous administration in adults (mean age 45.2 years). The continuous line represents the concentrations calculated by PK-Sim®, the dotted line those calculated by TIVA-Trainer.

FIG. 8 shows the predicted (lines) and experimental (symbols, data from Ickx B, Cockshott I D, Barvais L, Byttebier G, De P L, Vandesteene A et al. Propofol infusion for induction and maintenance of anaesthesia in patients with end-stage renal disease. Br J Anaesth 1998; 81(6):854-60.) blood propofol concentrations after intravenous administration in adults (mean age 45.2 years).

As a measure of the quality of the predicted plasma concentrations, the mean relative deviation (MRD) was calculated for the curves predicted with the PK-Sim® and the TIVA-Trainer in each case, using the following formula:

$$MRD = 10^{\sqrt{\frac{\Sigma(\log y - \log \hat{y})^2}{n}}}$$

In this equation, y represents the measured plasma concentrations, $\hat{y}$ the predicted plasma concentrations, and n the number of values measured.

The following MRD values were obtained for the curves shown in FIGS. 3 to 8:

TABLE 3

MRD values as a measure of the quality of the prediction of the plasma concentrations

| STUDY | MRD (TIVA-Trainer prediction) | MRD (PK-Sim ® prediction) |
|---|---|---|
| Raoof et al. | 1.20 | 1.34 |
| Saint-Maurice et al. | 1.20 | 1.29 |
| Valtonen et al. | 1.71 | 1.18 |
| Kanto et al. | 1.53 | 1.43 |
| Mertens et al. | 1.48 | 1.26 |
| Ickz et al. | 1.42 | 1.42 |
| TOTAL | 1.43 | 1.35 |

Taken together, FIGS. 3 to 8 and the calculated MRD values in Table 3 show that individual concentration/time courses of propofol can in most cases be predicted more accurately by the physiology-based model than with the conventional open three-compartment models.

In the next step, it is shown that the pharmacodynamic effect of propofol in different subpopulations can also be predicted more accurately by the physiology-based model PK-Sim® than by the conventional three-compartment model. A sensitive measure of the propofol effect is the time at loss of consciousness ($t_{LOC}$) after the start of a propofol infusion. The literature contains numerous values for $t_{LOC}$ in normal-weight and obese people, and in pregnant women. In this comparison, it should be borne in mind that the theoretical "concentrations" in the effect compartment calculated by TIVA-Trainer do not have the significance of a real concentration, as the effect compartment in the underlying three-compartment model does not have any physiological basis (in contrast to the active ingredient concentrations in the brain calculated by PK-Sim®). For this reason, it is not the absolute values which are of significance as a measure of the quality of the prediction, but the coefficients of variance of the brain or effect compartment concentration in various subpopulations.

Servin et al. (Servin F, Farinotti R, Haberer J, Desmonts J. Propofol infusion for maintenance of anesthesia in morbidly obese patients receiving nitrous oxide. Anesthesiology 2005; 78:657-65.) investigated the pharmacokinetics and pharmacodynamics of propofol in 8 obese and 10 normal-weight adults. The individual $t_{LOC}$ values, that is the time after the start of the propofol infusion when the patients lose consciousness, were reported in the study. For each of these patients, the propofol administration was simulated with PK-Sim® and TIVA-Trainer and the active ingredient concentrations in the brain (PK-Sim®) or concentration in the effect compartment (TIVA-Trainer) was calculated at the relevant time $t_{LOC}$. The relative standard deviation of these concentration values was determined as a measure of the quality of the prediction. In the case of the PK-Sim® simulations, the relative standard deviation of the active ingredient concentrations in the brain at the time of loss of consciousness was 27% in the normal weight population. Using the TIVA-Trainer model, the relative standard deviation of the concentration in the effect compartment for this population was 32%. In the obese population, the standard deviation determined with PK-Sim® was not substantially larger than in the normal-weight population (41%). With the TIVA-Trainer, by contrast, the standard deviation in the obese population was substantially larger, at 93%.

Another pharmacodynamic study by Kazama et al. (Kazama T, Ikeda K, Morita K, Kikura M, Ikeda T, Kurita T et al. Investigation of effective anesthesia induction doses using a wide range of infusion rates with undiluted and diluted propofol. Anesthesiology 2000; 92(4):1017-28) investigated the influence of different infusion rates of propofol in normal-weight adults. In this case, the relative standard deviations of the active ingredient concentrations in the brain calculated with PK-Sim® were 18%, that of the effect compartment concentrations with TIVA-Trainer was 21%.

As well as the time of loss of consciousness, the time of recovery of consciousness during emergence from anesthesia also correlates with the concentration of propofol. It is to be expected that the onset of and emergence from anesthesia would be associated with very similar active ingredient concentrations in the brain. As shown in Table 4, the active substance concentrations in the brain at the time of recovery of consciousness predicted by PK-Sim® (3.4 mg/l) are in very good agreement with the active ingredient concentrations in the brain at the time of loss of consciousness. These threshold values of concentration in the brain are in an absolute range from 2.2 to 4.0 mg/l. The concentration values in the effect compartment calculated by the TIVA-Trainer were 2.2 for the time of the recovery of consciousness and 1.0 to 1.6 for the simulated loss of consciousness, which represents a clear lack of agreement between the two values. In addition, PK-Sim® was able to predict the time of the minimum BIS value very accurately (relative deviation+8.3%), whereas the prediction of the Diprifusor model was out by a factor of almost 2.

TABLE 4

Pharmacodynamic endpoints predicted by PK-Sim ® and Diprifusor

| End point | Brain or effect concentration [mg/l] | | |
|---|---|---|---|
| | PK-Sim ® | Diprifusor | REFERENCE |
| Loss of consciousness | 3.1 | 1.6 | Kazama et al. |
| Loss of consciousness (children) | 2.9 | 1.1 | Valtonen et al. |
| Loss of consciousness (pregnant women) | 4.0 | 1.0 | Kanto et al. |
| Loss of consciousness (obese patients) | 2.7 | 1.3 | Servin et al. |
| Loss of consciousness | 2.2 | 1.3 | Servin et al. |
| Loss of consciousness | 2.9 | 1.1 | Kazama et al. |
| Loss of consciousness | 4.0 | 1.4 | Flaishon et al. |
| Mean (coefficient of variance) | 3.1 (21%) | 1.3 (16%) | |
| Recovery of consciousness | 3.4 | 2.2 | Flaishon et al. |
| Time to minimum BIS value (relative deviation from the actual value) | 117 s (+8.3%) | 212 s (+96.3%) | Flaishon et al. |

Now that it has been demonstrated in a series of practical cases that the physiology-based prediction of the propofol concentrations in plasma and at the site of action of the anesthetic on the basis of a physiology-based pharmacokinetic model is advantageous, the way in which this procedure can be used for the improvement of a system for the automatic control of an infusion pump will now be described.

Using the average active ingredient concentration in the brain of 3.5 mg/l corresponding to a BIS value of about 60 which was obtained above, it is possible to describe the nominal profile Z(t) of propofol in the brain. For reasons of safety, it is additionally possible to specify threshold values ($Z_{min}(t)$ and $Z_{max}(t)$) which must not be exceeded or fallen below during the period of anesthesia. In the case of values below the limit, there is a danger of the patient regaining consciousness during surgery, whereas in the case of values above the limit, adverse side effects cannot be ruled out.

A sensible nominal profile Z(t) is, for example, a rectangular profile for the active ingredient concentration in the brain with a plateau value of 3.5 mg/l of propofol during the period of anesthesia ($t_{anesth}$). The upper and lower limits are set to 3.0 mg/l and 4.0 mg/l in the brain. The time $t_{LOC}$ defines the desired time point at loss of consciousness. This gives the following function for the target profile Z(t):

$$Z(t) = \begin{cases} 0, & t < t_{LOC} \\ 3.5 \text{ mg/L}, & t_{LOC} \leq t \leq t_{anesth} \\ 0, & t > t_{anesth} \end{cases}$$

and $$Z_{min}(t) = \begin{cases} 0, & t < t_{LOC} \\ 3.0 \text{ mg/L}, & t_{LOC} \leq t \leq t_{anesth} \\ 0, & t > t_{anesth} \end{cases} \wedge$$

$$Z_{max}(t) = \begin{cases} 0, & t < t_{LOC} \\ 4.0 \text{ mg/L}, & t_{LOC} \leq t \leq t_{anesth} \\ 0, & t > t_{anesth} \end{cases}$$

Alternatively, a nominal profile for the BIS value can be defined directly.

In the next step, the infusion rate, i.e. the dose administered intravenously per time interval, is varied iteratively. The step width should sensibly be chosen such that it is appropriate to the distribution and elimination kinetics of the substance.

The simulation result obtained (=ACTUAL profile) is then compared with the NOMINAL profile. If a difference between the ACTUAL profile and the NOMINAL profile is outside the valid tolerance range, the quantity administered in the corresponding time step is varied until the entire ACTUAL profile agrees with the NOMINAL profile within the framework of the tolerance range. Suitable numerical optimization procedures here include gradient procedures, particularly quasi-Newton or Newton procedures, gradient-free procedures such as the nested-intervals procedure, and stochastic procedures such as the Monte-Carlo procedure for example. These dose profiles thus obtained are used in the last step of the inventive procedure as an input function to control a conventional automatic dose-metering unit, preferably an electronically controlled infusion pump.

The invention claimed is:

1. A computer-controlled device for time-controlled administration of an anesthetic, said device comprising:
   a) a module for inputting individual parameters of the patient and substance-specific input parameters of the anesthetic to be administered as well as a substance-dependent target profile, which shows a desired concentration/time course in the brain or a desired effect/time course administered as a function of time, connected to
   b) a physiology-based and/or pharmodynamic computer model module for a physiology-based pharmacokinetic and/or pharmacodynamic simulation of a dosage time profile which is variable over time taking into account the individual parameters of the patient and the substance-specific input parameters of the anesthetic to be administered, iterative numerical fit of the simulated dose profile until it agrees with the target profile or shows the maximum achievable agreement with it and output of an adapted dosage time profile, wherein the physiology-based and/or pharmodynamic computer model module is connected to
   c) a metered dose device controlled on the basis of the outputted adapted dosage time profile, and
   wherein the anesthetic is propofol.

2. The device as claimed in claim 1, wherein the anesthetic is administered to humans or animals.

3. The device as claimed in claim 1, wherein the fitting the dose profile uses one of the following numerical optimization procedures: gradient procedures, particularly quasi-Newton or Newton procedures; gradient-free procedures such as the nested-intervals procedure; stochastic methods such as the Monte-Carlo procedure.

4. The device as claimed in claim 1, wherein the therapeutic outcome can be monitored on-line using one or more suitable sensors and the measured signal or signals can contribute to the control of the dose metering device.

5. The device as claimed in claim 1, wherein the individual patient parameters to be taken into account comprise a selection of the following: body weight, age, body-mass index (BMI), blood flow rates, volumes and composition (proportion of water, fat and protein) of individual organs, gene expression data for metabolically active enzymes or active transporters.

6. The device as claimed in claim 5, wherein one or more anatomical, physiological and/or genetic parameters can vary over time.

7. The device as claimed in claim 5, wherein one or more anatomical, physiological and/or genetic parameters are measured in real time during administration.

* * * * *